United States Patent [19]

Mrsny et al.

[11] Patent Number: 4,879,220

[45] Date of Patent: Nov. 7, 1989

[54] CROSSLINKING RECEPTOR-SPECIFIC PROBES FOR ELECTRON MICROSCOPY

[75] Inventors: Randall J. Mrsny; G. Bruce Birrell; Johannes J. Volwerk, all of Eugene, Oreg.

[73] Assignee: State of Oregon Acting By and Through the State Board of Higher Education On Behalf of the University of Oregon, Eugene, Oreg.

[21] Appl. No.: 932,437

[22] Filed: Nov. 18, 1986

[51] Int. Cl.$^4$ ............................................. G01N 33/53
[52] U.S. Cl. ........................................ 435/7; 436/525; 436/526; 436/501; 424/3; 424/7.1; 435/6
[58] Field of Search ....................... 436/526, 525, 501; 424/3, 7.1; 435/7, 6

[56] References Cited

U.S. PATENT DOCUMENTS

| | | |
|---|---|---|
| 4,035,316 | 7/1977 | Yen et al. |
| 4,256,725 | 3/1981 | Rutner et al. |
| 4,313,734 | 2/1982 | Leuvering |
| 4,420,558 | 12/1983 | De Mey et al. |
| 4,446,238 | 5/1984 | De Mey et al. |
| 4,452,773 | 6/1984 | Molday |
| 4,552,812 | 11/1985 | Margel et al. |
| 4,735,796 | 5/1985 | Gordon ............................... 436/518 |
| 4,742,000 | 5/1986 | Greene ............................... 436/503 |

OTHER PUBLICATIONS

Leuvering et al., Journal of Immunological Methods, 62(1983)163–174.
Birrell et al., "Silver-Enhanced Colloidal Gold as a Cell Surface Marker for Photoelectron Microscopy," *J. Histochem. and Cytochem.* 34:339–345 (1986).
Birrell et al., "Immunophotoelectron Microscopy: The Electron Optical Analog of Immunofluorescence Microscopy,"*Proc. Natl. Acad. Sci. USA* 82:109–113 (1985).
DeMey, "Colloidal Gold as Marker and Tracer in Light and Electron Microscopy," *E.M.S.A. Bulletin* 14:54–66 (1984).
Hicks et al., "Localization of Lectin Receptors on Bovine Photoreceptor Cells Using Dextran-Gold Markers," *Invest. Opthalmol. Vis. Sci.* 26:1002–1013 (1985).
Horisberger, "Colloidal Gold as a Tool in Molecular Biology," *TIBS* (Nov. 1983), pp. 395–397.
Mrsny et al., "Potassium Ion Influx and Na$^+$, K$^+$-ATPase Activity Are Required for the Hamster Sperm Acrosome Reaction," *J. Cell Biol.* 91:77–82 (1981).
Mrsny et al., "Photoelectron Imaging of Guinea-Pig, Hamster and Human Spermatozoa," *J. Reprod. Fert.* 74:127–134 (1985).
Mrsny et al., "Hamster Sperm Na$^+$, K$^+$-Adenosine Triphosphatase: Increased Activity During Capacitation in Vitro and Its Relationship to Cyclic Nucleotides," *Biol. of Reprod.* 30:573–584, (1984).

Primary Examiner—Barry S. Richman
Assistant Examiner—Lyle Alfandary-Alexander
Attorney, Agent, or Firm—Klarquist, Sparkman, Campbell, Leigh & Whinston

[57] ABSTRACT

A method and probes are disclosed for the localization of functional receptors by electron microscopy (EM). Electron dense probes are directed to receptors by means of specific ligand-receptor interactions and subsequently anchored covalently to target cellular material. A particular probe is a complex between colloidal gold and dextran derivatized with diaminohexane and containing photo-activatable nitroarylazido groups. Ligands with a specific affinity for certain receptors can be covalently attached to the complex to provide receptor-specific markers. For example, ouabain can be covalently attached to the dextran matrix to produce a probe specific for functional units of Na,K-ATPase. Covalent attachment of the bound probes at or near their respective receptors greatly enhances retention of probe during washing and standard procedures of fixation and dehydration in preparation for EM.

39 Claims, 5 Drawing Sheets

CROSSLINKING RECEPTOR-SPECIFIC PROBES FOR ELECTRON MICROSCOPY

This invention was made with government support under Grant No. CA 11695, Grant No. GM 25698, and Fellowship No. GM 08712 awarded by the National Institutes of Health of the United States Public Health Service. The government has certain rights in this invention.

BACKGROUND OF THE INVENTION

The invention relates to probes suitable for ultrastructural localization by electron microscopy of receptors exposed at cell surfaces or present in intracellular membranes or other subcellular structures.

Knowledge of the architecture of cellular material is increasingly important to the understanding of biological systems. For example, characterization of the ultrastructural architecture of cell membranes is essential for a complete understanding of membrane function. New information concerning membrane function may provide the basis for novel drug design, therapies and diagnostic procedures.

A number of different approaches have been developed to obtain information concerning the number and localization of specific cellular components. Currently, cytochemical, immunocytochemical and radioligand techniques are the most widely employed to visualize the structure and dynamic events of membranes prior to and subsequent to some physiologic stimulus or cellular function. Each of these methods presents certain advantages and limitations but, particularly by combining the various methods, much information pertinent to the problem of membrane structure and function can be obtained.

Recently discovered techniques make EM a more useful tool for mapping cellular material. It is currently possible to purchase heavy-metal containing probes which have a large targeting protein, such as an antibody, a lectin, avidin or the like, to provide selectivity.

Colloidal gold particles are known to be useful as labels in EM studies as described by M. Horisberger in "Colloidal Gold as a Tool in Molecular Biology," *TIBS* (November 1983), pp. 395–397 and J. DeMey in "Colloidal Gold as a Marker and Tracer in Light and Electron Microscopy," E.N.S.A. Bulletin 14:54–66 (1984). Hicks and Molday in "Localization of Lectin Receptors on Bovine Photoreceptor Cells Using Dextran-Gold Markers," *Invest. Opthalmol. Vis. Sci.* 26:1002–1013 (1985), have observed that dextran derivatized with ethylenediamine readily binds to colloidal gold particles and can be used to form ligand-dextran-gold conjugates. U.S. Pat. No. 4,452,773 of Molday suggests that dextran can be used to coat colloidal sized iron particles which can be covalently bonded to antibodies for labeling cells or other biological materials.

Other patents in this field include U.S. Pat. No. 4,035,361 (Yen et al.) which discusses the production of polymeric microspheres with an attached lectin or antibody. Margel et al. discuss the formation of microspheres in U.S. Pat. No. 4,552,812. The patents of DeMey et al., U.S. Pat. Nos. 4,420,558 and 4,446,238 discuss the use of receptor-specific gold probes for bright field light microscopy. U.S. Pat. No. 4,313,734 (Leuvering) mentions the use of gold sols which are covered on the surface with antibodies as markers for EM, but primarily concerns the application of dispersed metal sol particles to determine the quantity of affinity bound components. Another assay method, that involves a labeled form of a ligand, is described in U.S. Pat. No. 4,256,725 (Rutner et al.).

It is known that Na,K-ATPase actively transports $K+$ and $Na+$ ions across plasmalemmal surfaces and therefore has a central role in the ionic and osmotic homeostasis of cells. Cytochemical, immunocytochemical and autoradiographic methods have previously been used to localize Na,K-ATPase. Ouabain is a selective inhibitor of Na,K-ATPase activity.

While existing immunogold markers can be used to label cellular material by attachment at receptor sites, methods based on cytochemical reaction products or radiography have severe limitations for EM visualization. Radioactive ligands used in autoradiography cannot be depended on to survive the washing, fixation and dehydration steps that are required to prepare biological materials for EM. For example, radiolabeled ouabain washes away under such conditions.

SUMMARY OF THE INVENTION

It has now been discovered that probes, with electron dense colloidal sized particles and receptor-specific structures, can be covalently anchored to their targets on a variety of cellular materials. This is accomplished by inducing cross-linking after the receptor-specific structure is connected with a receptor on the target cellular material. Particularly useful are probes based on a dextran/colloidal gold matrix to which receptor-specific ligands and crosslinking agents are attached by means of free amines in the matrix. Such probes take advantage of both the specificity of receptor/ligand interactions and the favorable properties of colloidal gold as an utlrastructural marker for electron microscopy.

A specific probe according to the present invention is capable of Na,K-ATPase localization at the utlrastructural level on intact human erythrocytes or human foreskin fibroblasts using transmission electron microscopy (TEM) or scanning electron microscopy (SEM). This probe, which includes a ouabain ligand, can be used to mark any type of cellular material that has an ouabain receptor.

It is an object of this invention to provide for the secure attachment of receptor-specific EM probes to target cellular material.

A specific object is to provide a probe for localizing Na,K-ATPase at the external surfaces of cells.

Another object is to provide a series of multi-purpose probes which can be used to target receptors on a wide variety of tissues and organisms.

DETAILED DESCRIPTION

Figure 1:
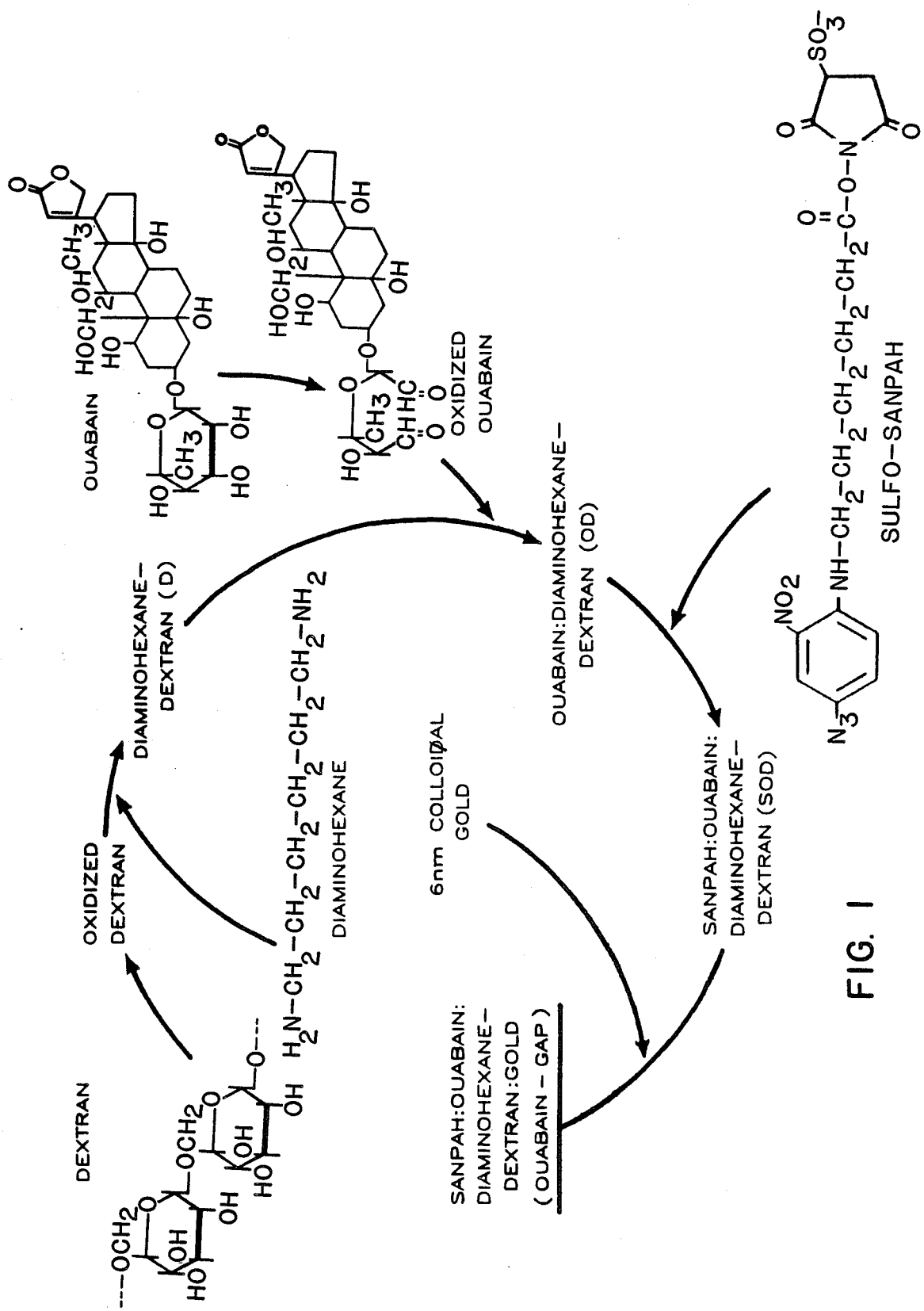
FIG. 1 is a schematic diagram of the synthetic route followed to obtain the gold-affinity probe ouabain-GAP and the intermediate product, glucose-GAP, which is synthesized by omitting the step in which oxidized ouabain is attached.

According to the present invention, a probe is provided that is suitable for attachment to a receptor located, e.g., on the surface of or within a cell. As used herein, "receptor" is defined as any molecule or complex of molecules of biological origin for which there is a ligand binding specifically to the molecule or complex of molecules.

The probe includes a colloidal sized particle having a diameter of about 20 to 1500 Å, more particularly about 20 to about 600 Å. For use of the probe in EM, the colloidal sized particle must be made of an electron dense material, most preferably, gold or some other heavy metal. Polystyrene beads are also suitable.

The probe also includes a receptor-specific structure or "ligand" identifier which targets specific receptors of the cell. The ligand is derivatized, if needed, for attachment to the colloidal particle by means of a polymer. In the following examples, the ligands are ouabain, a cardiac glycoside which selectively binds with the plasma membrane Na,K-ATPase (ATP phosphohydrolase, EC 3.6.1.3), and terminal D-glucose residues, which bind selectively with glucose transporters. Other receptors could be targeted by probes which contain ligands or derivatives of ligands such as biogenic amine neutrotransmitters (serotonin, epinephrine, norepinephrine, acetylcholine etc.), neurologically active amino acids (glutamate, aspartate, taurine etc.), neuropeptides (endorphins, enkephalins etc.), hormones (oxytocin, insulin, cortisone, prostaglandis, platelet activating factor etc.), growth factors (somatomedins, epidermal growth factor etc.), ion channel blockers (tetrodotoxin, saxitoxin etc.), enzyme substrates (ATP and other nucleotides) or inhibitors, drugs (e.g., ciclosporine, 5-fluorouracil, azidothymidine), and tumor promoters (phorbol esters). In addition, oligonucleotides or complementary DNA fragments could be attached to the polymer-colloidal particle matrix providing probes that could be used for genomic mapping. The low molecular weight ligands are particularly useful because they attach to receptors on numerous types of tissue from many species of origin.

The ligand is attached to a colloidal particle by a polymer having a functional group suitable for attachment of the ligand. Most advantageously, the colloidal particles can be covered with a polysaccharide or a polysaccharide-derivative having pendant functional groups, particularly a derivative of dextran, as described in U.S. Pat. No. 4,452,773 (Molday).

Although the probes described below utilize dextran derivatized with diaminohexane to coat the colloidal particles, use of other polymers can be anticipated. These can be of biological origin, for example polysaccharides or proteins such as serum albumin or gelatin, or synthetic polymers. Copolymers of amino acids, containing lysine residues, may be suitable.

In general, to be useful for the construction of probes as described herein, a polymer should have the following properties: (1) The polymer should be water soluble with a molecular weight preferably in the range of 20 to 100 kD, although use of polymers with molecular weights outside this range is not excluded. (2) The polymer should contain a sufficient number of functional groups such as mines to allow for covalent attachment of receptor-specific ligands and crosslinking moieties. (3) The polymer should bind (essentially irreversibly) to colloidal particles after ligands and crosslinking agents are attached.

Dextran has terminal D-glucose residues and thus intrinsically binds selectively to glucose transporters. To target another receptor, the polysaccharide can be formulated so that it includes one of the identifiers or derivatives mentioned above. The identifier can be attached by means of a linker arm that extends from the polysaccharide and terminates in either a primary amine or another reactive functional group. A diamino-alkane, such as diaminohexane, is preferred for forming linker arms attached to dextran derivatives.

A unique aspect of this invention is a provision for the probe to be bound to the target not only by interaction of the ligand with the receptor, but also by crosslinking, i.e. creating one or more covalent linkages directly between the receptor and the probe. Such a probe may be formed to include a crosslinking agent which can be induced to react, at a desired time, to form covalent bonds with the target cellular material.

In general, a suitable crosslinking agent should have the following properties: (1) It should be heterobifunctional, i.e., contain two different reactive functional groups. One of these functional groups should be such that the crosslinking agent can be attached to the polymer coating the colloidal particle, while the reactivity of the second functional group remains intact. (2) The reactivity of the second functional group should be induceable by the application of an external stimulus, for example by photo-activation or by changing parameters such as pH and temperature or by addition of another reagent.

Suitable crosslinking agents include heterobifunctional photoactivatable nitrene-generating crosslinkers such as sulfo-SANPAH, N-5-Azido-2-nitrobenzoyloxysuccinimide and sulfosuccinimidyl 2-(m-azido-o-nitrobenzamido)-ethyl-1,3-dithiopropionate. The latter compound contains a cleavable disulfide linkage which would allow separation of a covalently attached receptor from the probe. After the probe receptor complex has been isolated, the receptor can be separated from the complex by the addition of a reducing agent such as dithiothreitol. Other suitable crosslinking agents include photoactivatable carbene-generating crosslinkers such as p-nitrophenyl-2-diazo-3,3,3-trifluoropropionate and 2-diazo-3,3,3-trifluoropropionylchloride and crosslinking agents such as glutaraldehyde or other dialdehydes, and dimethyl adipimidate (DMA) and dimethyl suberimidate (DMS) might be useful in specific cases where these agents can be added as an additional component. These agents can also be bound to the polysaccharide by means of diaminohexane or a similar linker arm compound.

As illustrated by the example below, a radiation activatable crosslinking agent, such as SANPAH, can be attached to the probe prior to brining the probe into contact with a cell surface or other target. The example shows attachment by a polymer having a functional group suitable for attachment of the crosslinking agent to the colloidal sized particle of the probe.

After the probes are attached and crosslinked, the sample is washed, fixed with glutaraldehyde and dehydrated by the normal procedures used to prepare specimens for EM. Probes connected with such crosslinking agents have a dramatically better retention rate than probes without such agents.

The following example describes probes which localize receptors at the external surfaces of cells. The human erythrocytes and fibroblasts described therein provide test systems which allow for comparison of probe distribution by both TEM and the more surface-oriented technique of SEM. TEM of thin sections detects probe particles attached anywhere to cellular material, while SEM detects only those at the upper surface of cells.

Analogous probes could be used to label such interior features of cells as cytoskeletal proteins intracellular organelles and DNA. Such probes could be transported to the interior of a cell by microinjection [Mangeat et al., *Techniques in Immunocytochemistry*, Vol. 3, Bullock, G. R. and Petrusz, P. Eds., (Acad. Press, London 1985), pp. 79-96] or the cell wall could be permeabilized to allow osmotic transport of probes to the cell interior. In some instances, the cell wall could be removed by a detergent, whereafter the cell contents could be brought into contact with the probes.

An additional feature of this invention is the use of the probes described herein to isolate molecules or complexes of molecules. The probes can be attached to target molecules and then crosslinked to form secure bonds. Thereafter, a separation technique which acts on a physical parameter of the probe (e.g. density, size, or magnetic attraction) can be employed to isolate the probes which bear the target molecules. Chemical reagents can then be used to separate the probes from the target molecules, such that the target molecules or complexes are isolated in what is essentially a single step.

Abbreviations used herein include the following:

Sulfo-SANPAH is sulfosuccinimidyl-6(4'-azido-2'-nitrophenylamino) hexaoate;
FDNB is 1-fluoro-2,4-dinitrobenzene;
BSA is bovine serum albumin;
HETLC is high efficiency thin layer chromatography;
D is dextran derivatized with 1,6-dimaminohexane;
OD is conjugate of D and oxidized ouabain;
SD is conjugate of D and sulfo-SANPAH;
SOD is conjugate of OD and sulfo-SANPAH;
GAP is gold-affinity probe;
Glucose-GAP is 6 nm colloidal gold coated with SD;
Ouabain-GAP is 6 nm colloidal gold coated with SOD;
PSB is 5 mM $NaPO_4$ (pH 8.0) containing 150 mM NaCl;
HBS is 50 mM Hepes (pH 7.2) containing 3.4 mM $CaCl_2$, 6.7 mM KCl, 0.6 mM $MgSO_4$ and 137 mM NaCl; and
SDS-PAGE is sodium dodecylsulfate-polyacrylamide gel electrophoresis.

EXAMPLE

This example describes the preparation, characterization and application of two probes according to the present invention that employ a photo-activated crosslinker for covalent anchoring of the probes which have been joined to receptors on cell surfaces.

A first probe, specific for D-glucose transport complexes, comprises a colloidal gold particle in a matrix of dextran which has terminal glucose residues. A second probe, specific for Na,K-ATPase, was obtained by chemically linking the ATPase inhibitor, ouabain, to a dextran/colloidal gold matrix.

Both probes were used for localization of their respective receptors at the plasma membranes of human erythrocytes and cultured human foreskin fibroblasts. Retention of the probes, during fixation and dehydration in preparation of the labeled cells for electron microscopy, was found to be dramatically improved when the dextran-gold matrix was anchored by the crosslinking agent.

EXPERIMENTAL PROCEDURE

Materials. Ouabain octahydrate was obtained from Calbiochem of San Diego, California, U.S.A., and [21,22-$^3$H]-ouabain (specific activity 16 Ci/mmol) was from Amersham Corp. of Arlington Heights, Illinois, U.S.A. Sulfo-succinimidyl-6(4'-azido-2'-nitrophenylamino) hexanoate (sulfo-SANPAH) was from Pierce Chemical Co. of Rockford, Ill., U.S.A.; $NaIO_4$ was from J. T. Baker of Phillipsburg, N.J., U.S.A.; 1-fluoro-2,4-dinitrobenzene (FDNB) was from Matheson, Coleman and Bell of East Rutherford, N.J., U.S.A. Anhydrous D-glucose was from Mallinckrodt, Inc. of St. Louis, Mo., U.S.A. Bovine Serum Albumin (fraction V, fatty acid poor) and dextranase (*Chaetomium gracile*) were from Miles Laboratories of Elkhart, Ind., U.S.A. Thin-layer chromatography (TLC) plates from Analtech, Inc. of Newark, Del., U.S.A. (HETLC-GHL) were preeluted with diethyl ether and heat reactivated at 140° C. for two hours prior to use. Spectrapor membrane dialysis tubing (6,000–8,000 M.W. cut off) was from Spectrum Medical Industries of Los Angeles, Calif., U.S.A. Parlodion was from Ernest F. Fullam, Inc. of Latham, N.J., U.S.A. Glutaraldehyde (E.M. grade, 8 percent aqueous) was from Polysciences, Inc. of Warrington, Pa., U.S.A. Poly-L-lysine (type II, 4,000 ave. M.W.), cytochalasin B (*Helminthosporium dematioideum*), QAE Sephadex Q-25-120, dextran (40,000 ave. M.W.), 1,6-diaminohexane, $N^e$-2,4-dinitrophenyl-l-lysine and cold water fish gelatin were from Sigma of St. Louis, Mo., U.S.A. Other chemicals used were of the highest quality available.

Probe Preparation and Characterization (FIG. 1). Dextran (1 g) and $NaIO_4$ (0.16 g) were dissolved in 5 ml of 0.1 M sodium acetate (pH 5.0) and stirred for 1.5 h at 25° C. [Hicks and Molday, "Localization of Lectin Receptors on Bovine Photoreceptor Cells Using Dextran-Gold Markers," *Invest. Ophthalmol. Vis. Sci.* 26:1002–1013 (1985)]. Following dialysis against water at 4° C., 1,6-diaminohexane (1 g) dissolved in 1 ml of water was added and the pH was brought to 9.5 with concentrated HCl. The solution was stirred at 25° C. for 5 min, 120 mg sodium borohydride was added and stirring was continued for 1 h at 25° C. The product, dextran derivatized with diaminohexane via reductive amination (D), was dialyzed against water and lyophylized.

The free amine content of D was estimated based on the procedure of Sanger and Tuppy, "The Amino-Acid Sequence in the Phenylalanyl Chain of Insulin. 1. The Identification of Lower Peptides from Partial Hydrolysates," *Biochem. J.* 49:463–490 (1951) using FDNB. D (10–25 mg) was dissolved in 0.5 ml of 0.5 M $NaHCO_3$ (pH 8.5) and 0.1 ml ethanol and 75 µl FDNB were added. After 3 h of vigorous stirring at room temperature, the mixture was centrifuged to remove excess FDNB and a small precipitate and the supernatant was exhaustively dialyzed against distilled water. The dinitrophenylated derivatized dextran was lyophilized, weighed and dissolved in a known volume of water. The free amine content of D (number of $NH_2$ groups per polymer of average MW 40,000) was then calculated from the absorbance at 360 nm using the molar extinction coefficient determined for $N^e$-DNP-lysine ($E_{360} = 17,070 \text{ M}^{-1}\text{cm}^{-1}$).

Preparation of the Na,K-ATPase-specific probe required covalent attachment of oxidized ouabain to a D via reductive amination. Due to the light-sensitive nature of ouabain and sulfo-SANPAH, all subsequent steps were performed in the dark using a safe-light or in subdued lighting. To generate oxidize ouabain, 10 mM aqueous ouabain was mixed with an equal volume of a freshly prepared 100 mM aqueous solution of $NaIO_4$ [Rossi et al., "Affinity Labeling of the Digitalis Receptor with p-Nitrophenyltriazene-Ouabain, a Highly Specific Alkylating Agent," *J. Biol. Chem.* 255:9936–9941 (1980)]. Ouabain oxidation was complete by 24 h of stirring at room temperature and verified by TLC using the solvent system of chloroform:methanol:water (10:5:1). Detection of ouabain and oxidized ouabain was performed using a sterol-specific stain [Lowry, "Ferric Chloride Spray Detector for Cholesterol and Cholesterol Esters on Thin-Layer Chromatograms" *J. Lipid Res.* 9:397 (1968)]. The reaction mixture was desalted using a QAE Sephadex Q-25-120 column, and the lyophylized oxidized ouabain was stored at −20° C.

Oxidized [$^3$H]-ouabain was similarly prepared. Briefly, 0.125 mCi [21,22-$^3$H]-ouabain was diluted with 50 mg cold ouabain and dissolved in 5 ml water. $NaIO_4$ (0.1426 g) dissolved in 5 ml water was added and the mixture was stirred at room temperature. After 3 h TLC indicated complete conversion of the ouabain into its oxidation products. Work up as described above gave 49 mg of oxidized [$^3$H]-ouabain with a specific radioactivity of $0.516 \times 10^6$ cpm/$\mu$mol.

Coupling of the oxidized ouabain to D was performed by dissolving 40 mg of oxidized ouabain and 50 mg D in 2.5 ml of 100 mM $NaPO_4$ (pH 6.5). After addition of 25 mg sodium cyanoborohydride, the mixture was stirred at 4° C. for 24 h and again after a second addition of 25 mg cyanoborohydride. The ouabain-derivatized dextran complex (OD) was dialyzed against 10 mM $NaPO_4$ (pH 7.4) containing 10 mM $NaN_3$. Oxidized [$^3$H]-ouabain was used to estimate the extent of incorporation of ouabain into the derivatized dextran (number of ouabain residues per polymer of average MW 40,000) under these reaction conditions.

The 6(4'-azido-2'U -nitrophenylamino) hexanoly (SANPAH) of photo-activated crosslinker sulfo-SANPAH was attached at the free amines of D or OD to produce SANPAH-dextran (SD) or SANPAH-ouabain-dextran (SOD), respectively. D or OD (100 mg) and 12.5 mg of sulfo-SANPAH were dissolved in 15 ml of 10 mM $NaPO_4$ (pH 8.0) and stirred in the dark for 24 h at 4° C. Unreacted sulfo-SANPAH was removed by dialysis against 10 mM $NaPO_4$ (pH 7.4) or by gel filtration on Sephadex G-25. The SANPAH content of SD or SOD (number of SANPAH residues per polymer of MW 40,000) was estimated from the absorbance at 475 nm of an aqueous solution of SD or SOD of known concentration using the molar extinction coefficient determined for sulfo-SANPAH ($E_{475} = 4290 \text{ M}^{-1}\text{cm}^{-1}$).

Coating colloidal gold particles with SD or SOD was the final step in the preparation of the glucose-GAP and ouabain-GAP labels, respectively. Colloidal gold particles (averaging approximately 6 nm in diameter) were prepared by citrate-tannic acid reduction of $HAuCL_4$ [Slot and Geuze, "A New Method of Preparing Gold Probes for Multiple-Labeling Cytochemistry," *Eur. J. Cell Biol.* 38:87–93 (1985)] and mixed with SD or SOD at pH 7.0. Optimal ratios of SD or SOD to colloidal gold, determined by a saturation test [Horisberger and Rosset, "Colloidal Gold. A Useful Marker for Transmission and Scanning Electron Microscopy," *J. Histochem. Cytochem.* 25:295–305 (1977)], performed in the presence of $H_2O_2$ to eliminate interference by tannic acid. Following addition of the predetermined amount of SD or SOD to the colloidal gold solution and a 10 min incubation, enough of 2 mM $NaBO_3$ (pH 9.0) containing 10 percent BSA was added to produce a final BSA concentration of 1 percent, the BSA acting as a stabilizer for the gold complexes. Glucose-GAP and ouabain-GAP were isolated by centrifugation (1.5 h at 40,000 rpm in an SW 41 rotor) into a step gradient. The gradient steps consisted of 1 ml volumes of 20 percent, 40 percent and 60 percent glycerol in 10 mM $NaPO_4$ (pH 7.4) containing 150 mM NaCl, 10 mM $NaN_3$ and 1 percent BSA which were layered on top of 0.5 ml of a 100 percent glycerol cushion. Probe banding in the 40–60 percent glycerol steps was removed and dialyzed against 10 mM $NaPO_4$ (pH 7.4) containing 150 mM NaCl and 10 mM $NaN_3$. To ensure complete removal of noncomplexed SD or SOD and residual tannic acid, the centrifugation procedure was repeated once more. Glycerol was then removed by exhaustive dialysis against the 10 mM $NaPO_4$ buffer and the gold complex was concentrated in an Amicon ultrafiltration cell using a YM-10 membrane to an $OD_{520}$ of approximately 1.0. When stored at 4° C. in the presence of 10 mM $NaN_3$, both probes were stable for at least several months, as judged by the criteria of unaltered capacity to label cells and by the absence of clumped colloidal gold particles upon inspection by TEM.

The stoichiometry of the ouabain-GAP complex (number of SOD polymers per colloidal gold particle) was estimated using radioactive SOD. A series of test tubes were prepared each containing 0.273 nmol 6 nm colloidal gold particles in 5 ml of 2 mM sodium phosphate buffer (pH 7.0). The particle concentration of the colloidal gold was calculated from the known starting amount of $HAuCl_4$ assuming complete reduction to 6 nm colloidal gold. Varying amounts of S[$^3$H]-OD (specific radioactivity $0.32 \times 10^6$ cpm/umol) were added to test tubes to give a final molar ratio of S[$^3$H]-OD to colloidal gold particles between 0.8 and 5. After a 10 min incubation, the mixtures were transferred to centrifuge tubes and spun for 2 h at 40,000 rpm in a SW 50.1 rotor to precipitate the colloidal gold with associated S[$^3$H]-OD. The supernatant were collected, lyophylized, dissolved in 1 ml water and the total radioactivity remaining was determined by liquid scintillation counting. From these data, the average number of SOD polymers bound to a single 6 nm colloidal gold particle was estimated.

Cell Preparation and Labeling. Human erythrocytes were isolated from freshly drawn whole blood by repeated washing in 5 mM $NaPO_4$ (pH 8.0) containing 150 mM NaCl (PBS) taking care to remove buffy coat contaminants [Steck, "Preparation of Impermeable Inside-Out and Right-Side Out Vesicles from Erythrocyte Membranes," *Methods and Membrane Biolog.*, Vol. 2 (Plenum Press, New York, 1974), pp. 245–281]. For labeling studies with glucose-GAP, 0.5 ml of erythrocytes (diluted with PBS to 5 percent hematocrit) was combined with 0.5 ml of glucose-GAP and 0.5 ml of either PBS (experimental) or PBS containing 600 mM glucose or 6 uM cytochalasin B (controls). For ouabain-GAP labeling, 0.5 ml volumes of erythrocytes and ouabain-GAP were combined with 0.5 ml of PBS containing either 600 mM glucose (experimental) or 600 mM glucose plus 3 mM ouabain (control). After incubation at 37° C. for 45 min in the dark, the cells were washed with PBS. A small volume of each treated erythrocyte preparation was then placed on a polylysine-coated glass disc and the cells were allowed to adhere for 15 min. The discs were then washed with PBS to remove unadhered cells, placed in a drop of PBS and irradiated on ice for 15 min using a HBO 200 W Hg short-arc lamp (Osram) at a distance of 20 cm. Control experiments with SOD showed that under these conditions photolysis was complete in less than 15 min as judged by the absence of any further changes in the absorption spectrum.

Human foreskin fibroblasts were cultured to subconfluency on glass discs placed in culture dishes using Dulbecco's modified Eagle's medium (Gibco Laboratories, Grand Island, NY, U.S.A.). For labeling with glucose-GAP, glass discs with attached fibroblasts were removed from the culture dishes and washed twice with HBS. The cells were then exposed to fresh HBS (experimental) or HBS containing 400 mM glucose or 0.4 uM cytochalasin B (controls) for 5 min at room temperature. Next, an equal volume of glucose-GAP, containing 1 percent fish gelatin [Birrell et al., "Silver-Enhanced Colloidal Gold as a Cell Surface Marker for Photoelectron Microscopy," *J. Histochem. Cytochem.* 34:339–345 (1986)] was added to all samples and after 5 mins in the dark at room temperature unbound glucose-GAP was removed by rinsing three times with HBS. The discs were then placed in a drop of HBS and irradiated on ice as described above for erythrocytes. For labeling with ouabain-GAP cells grown in culture dishes were washed twice with HBS and exposed to HBS containing 400 mM glucose (experimental) or HBS containing 400 mM glucose plus 2 mM ouabain (control) for 15 min at 37° C. An equal volume of ouabain-GAP was then added followed by incubation for 30 min in the dark at room temperature. At this point, the presence of ouabain or ouabain-GAP caused the cells to detach from the substrate. The cells were recovered and unbound probe was removed by centrifugation in HBS. Cells were resuspended in fresh HBS and irradiated for 15 min in a water-jacketed cell at 4° C. using the light source described above.

Fixation of samples was performed by slowly adding an 8 percent aqueous glutaraldehyde solution to a final concentration of 1 percent. After 1 h at room temperature samples were washed twice with water to remove excess fixative. Cells fixed in suspension were allowed to adhere to 5 mm diameter glass discs that had been previously glow-discharged or coated with poly-L-lysine at pH 13 to facilitate attachment of the cells.

Silver Enhancement. Marker resolution was improved via silver enhancement of the gold particles. The procedure of Birrell et al. (1986), supra, was used for SEM samples except that longer enhancement times were used; approximately 15 min for human erythrocytes and 30 min for fibroblasts.

Microscopy. Following attachment to glass discs and silver enhancement, ouabain-GAP labeled fibroblasts and all erythrocyte samples were dehydrated through a graded series of acetone and air-dried. Fibroblasts labeled with glucose-GAP were dehydrated through a graded series of ethanol, transferred to Freon and air-dried. Samples to be viewed by SEM were mounted on SEM stubs and putter coated with Au:Pd. Preparations were examined in an AMR 1000 scanning electron microscope at an operating voltage of 30 kV. Samples to be viewed by TEM were postfixed in 2 percent buffered $OsO_4$, washed and dehydrated through a graded series of ethanol/$H_2O$ solutions. Samples were sedimented into Epon/Araldite and polymerized. Ultrathin sections (approximately 70 nm) were stained with 5 percent uranyl acetate (20 min) and Reynold's ["The Use of Lead Citrate at High pH as an Electron Opaque Stain in Electron Microscopy," *J. Cell Biol.* 17:208–211 (1963)] lead citrate (1 min). Sections were viewed in a Philips EM-300 electron microscope.

Isolation of Membrane Components Attached to the Probes. Human foreskin fibroblasts grown to subconfluency in culture dishes were labeled with glucose-GAP as described previously. Following washing and irradiation on ice, the fibroblasts were solubilized in 0.1 percent SDS. Cellular components covalently attached to the colloidal gold probe were collected by centrifugation at 100,000×g for 1 h at 25° C. The colloidal gold pellet was resuspended in 10 ml of 0.1 M $KPO_4$ at pH 5.5 containing 0.02 percent $NaN_3$ and 170 units of dextranase. After incubation for 1 h at 40° C., the sample was dialyzed at 4° C. against water and lyophilized. The resuspended sample was analyzed for polypeptide composition by SDS-PAGE [Laemmli, "Cleavage of Structural Proteins During the Assembly of the Head of Bacteriophage T4, " *Nature* (Lond.). 227:680–685 (1970)]. A similar experiment was performed with human foreskin fibroblasts labeled with ouabain-GAP. Controls omitting the dextranase treatment were run in parallel.

RESULTS

Probe Preparation and Characterization. The synthetic steps for preparation of the Na,K-ATPase-specific probe ouabain-GAP are diagrammed in FIG. 1. The glucose transporter-specific probe (glucose-GAP) was similarly prepared except that the reaction with oxidized ouabain was omitted. Reaction of diaminohexane with oxidized dextran results in incorporation of an average of 12–15 free amino groups per dextran monomer of approximately 40,000 MW, as determined by reaction with FDNB. None of the free aldehydes [measured by reaction with 2,4-dinitrophenylhydrazine as described by Siggia and Hanna in *Quantitative Organic Analysis Via Functional Groups,* 4th Ed. (Wiley-Interscience, New York, 1979) pp. 148–152] originally present in the oxidized dextran remain after reaction with diaminohexane. The order of addition of diaminoheane and the reducing agent, sodium borohydride, is important since essentially no free amines could be detected when sodium borohydride was added first.

Under the conditions used here, 5–7 of the free amines of dextran derivatized with diaminohexane react with oxidized ouabain as determined by measuring the incorporation of oxidized [$^3$H]-ouabain. This number could be decreased or increased in a straight-forward manner by adjusting the molar ratio of ouabain to dextran in the reaction mixture. The remaining free amines were converted quantitatively into the corresponding SANPAH derivatives by reaction with a small excess of sulfo-SANPAH resulting in a product (SOD) containing 5-7 ouabain and 8-10 SANPAH residues per dextran polymer of MW 40,000. Two different glucose-GAP preparations were used; one contained approximately 5.5 and the other 8.5 residues of SANPAH per polymer of MW 40,000. There was no difference in the labeling observed with these two preparations.

Using SOD prepared with [$^3$H]-ouabain, the ouabain-GAP complex was found to contain approximately 4 SOD polymers per colloidal gold particle of 6 nm diameter. The ouabain-GAP probe therefore contains approximately 20-30 ouabain (receptor-specific ligand) residues and 30-40 SANPAH (photoaffinity ligand) residues per colloidal gold particle. Probes were typically prepared and stored at an $OD_{520}$ of 1.0 which equals a colloidal gold concentration of approximately $1.6 \times 10^{13}$ particles/ml [Horisberger, "The Gold Method as Applied to Lectin Cytochemistry in Transmission and Scanning Electron Microscopy," in *Techniques in Immunocytochemistry*, Vol. 3, G. R. Bullock and P. Petrusz, editors. (Academic Press, New York, 1985), pp. 155-178]. For ouabain-GAP this corresponds to a total ouabain concentration of approximately 0.5 $\mu$M.

Neither dextran itself nor oxidized dextran binds efficiently to colloidal gold as judged by the saturation test, i.e., protection against salt-induced flocculation of the gold sol (Hicks and Molday, "Localization of Lectin Receptors on Bovine Photoreceptor Cells Using Dextran-Gold Markers," *Invest. Opthalmol. Vis. Sci.* 26:1002-1013 (1985). Introduction of amino groups dramatically improves the binding of dextran to colloidal gold and this improved binding is retained following particular or complete derivatization of the free amines with ouabain and/or SANPAH.

At a concentration corresponding to a total ouabain concentration of 0.1 $\mu$M, ouabain-GAP was found to inhibit the Na,K-ATPase activity of a microsomal preparation of dog kidney cortex [Schoner et al., "On the Mechanism of Na$^+$- and K$^+$-Stimulated Hydrolysis of Adenosine Triphosphate," *Eur. J. Biochem.* 1:334-343 (1967)] similar to the inhibition observed in the presence of 0.1 $\mu$M free ouabain (J. Widdecombe, University of California at San Francisco, personal communication). Inhibition was dependent on the presence of the ouabain moiety since addition of glucose-GAP had no effect while addition of SOD produced inhibition similar to that of ouabain-GAP. SOD also inhibited the transepithelial short circuit current ($I_{sc}$) across cultured monolayers of dog trachea epithelial cells plated at $10^6$ per cm$^2$ onto Nucleopore filters placed in a conventional Ussing chamber [Widdecombe et al., "Cystic Fibrosis Decreases the Apical Membrane Chloride Permeability of Monolayers Cultured for Cells of Tracheal Epithelium", *Proc. Natl. Acad. Sci. U.S.A.* 82:6167-6171 (1985)]. A response similar to that of native ouabain was obtained when SOD was added from the serosal side of the cultured monolayer. No effect was observed when SD was added to the serosal side or when SOD was presented to the mucosal side of the cultured monolayer (J. Widdecombe, University of California at San Francisco, personal communication). These results suggest that SOD and the corresponding ouabain-GAP probe interact specifically with Na,K-ATPase in a manner similar to that of native ouabain, i.e., by inhibiting enzyme activity and inducing subsequent alterations of cell function.

Figure 2:
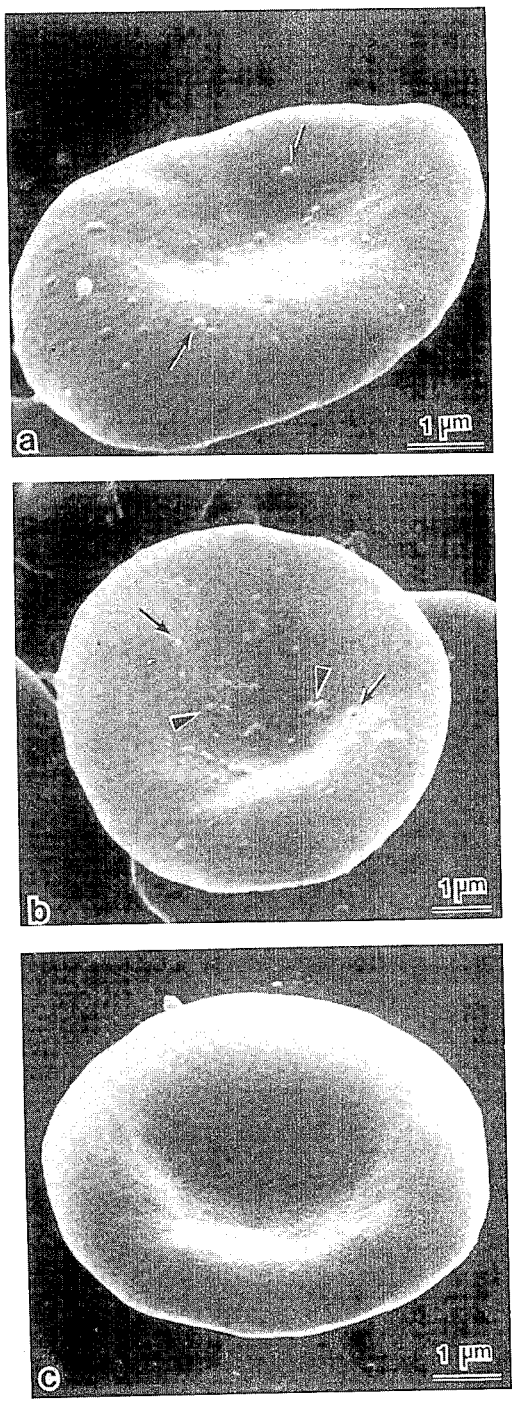
FIGS. 2 are scanning electron micrographs of human erythrocytes labeled with glucose-GAP (a) or ouabain-GAP (b), and a control erythrocyte (c) for ouabain-GAP labeling where competing ligand was presented simultaneously to probe.

Labeling of Human Erythrocytes. SEM micrographs of intact human erythrocytes labeled with the glucose transporter-specific probe (glucose-GAP) or the Na,K-ATPase-specific probe (ouabain-GAP) are shown in FIGS. 2a and 2b, respectively. Labeling with glucose-GAP was blocked in the presence of glucose or cytochalasin B, while labeling with ouabain-GAP was blocked in the presence of glucose plus ouabain as shown in FIG. 2c for glucose-GAP and glucose. This effect of added competing ligands indicates that the observed labeling is selective and dependent on specific interaction between the ligand attached to the colloidal gold/dextran matrix and the receptor. Erythrocytes labeled with glucose-GAP (followed by silver enhancement of the bond colloidal gold particles to more readily detect attached probe) showed a random distribution of probe with approximately 40-50 probe particles visible per cell (FIG. 2a). A more or less random distribution of silver-enhanced probe was also observed after labeling with ouabain-GAP with approximately 50-75 probe particles visible per cell (FIG. 2b). Larger particles, may represent small clusters of colloidal gold particles that have been fused together during silver enhancement.

Figure 3:
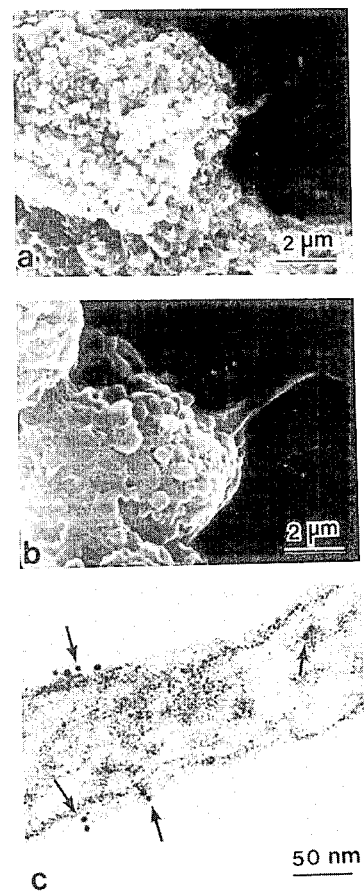
FIGS. 3 are scanning electron micrographs (a and b) and a transmission electron micrograph (c) of human foreskin fibroblasts labeled with ouabain-GAP.

Labeling of Fibroblasts. Scanning electron micrographs of fibroblasts labeled with ouabain-GAP in the absence or presence of excess competing ligands (ouabain) are shown in FIGS. 3a and 3b, respectively. Here, exposure to ouabain-GAP or ouabain caused the cells to lift from the substrate and take on a rounded morphology rather than the spread appearance that is characteristic of cultured fibroblasts. The density of ouabain-GAP label is rather high for these cells which may explain the appearance of the probe particles as wafers of silver rather than piles like those observed in FIG. 2 following silver enhancement. Distribution of unenhanced probe was demonstrated by thin section transmission electron microscopy. Here, a fibroblast microvillus labeled with ouabain-GAP shows a partially clustered array of colloidal gold particles, as indicated by arrows, at the membrane surface (FIG. 3c).

Figure 4:
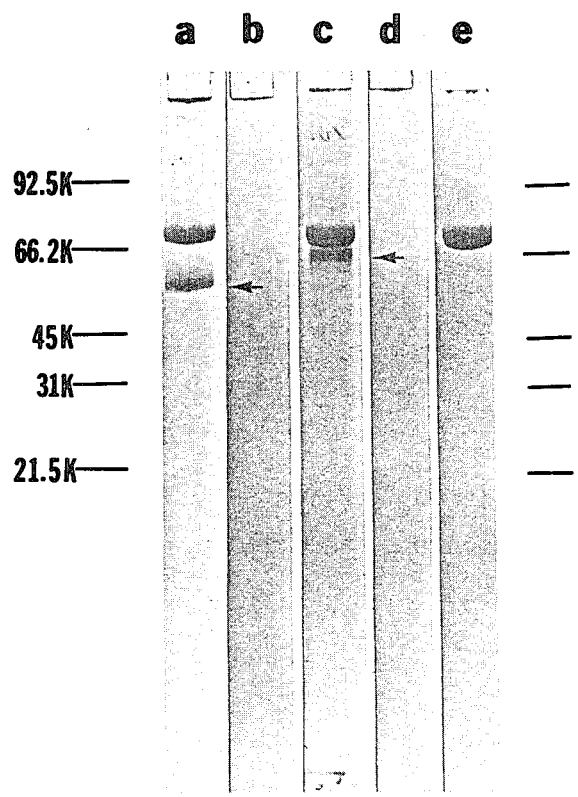
FIG. 4 shows SDS polyacrylamide gel electrophoresis of cell surface components covalently coupled to glucose-GAP and ouabain-GAP probes.

Isolation of Membrane Components Attached to Glucose-GAP or Ouabain-GAP. FIG. 4 shows an SDS-PAGE of protein components covalently attached to probes by affinity-gold labeling of human foreskin fibroblasts.

Following photolysis and solubilization with 1 percent SDS, glucose-GAP or ouabain-GAP probes were collected by centrifugation at 100,000×g. Release of the colloidal gold moiety from the polypeptides covalently attached to the glucose-GAP or ouabain-GAP probes was performed with dextranse prior to electrophoresis on an 8.75 percent slab gel. Coomassie Blue was used to visualize the isolated polypeptides. The molecular weight markers indicated are: phosphorylase b (92,500), bovine serum albumin (66,200), ovalbumin (45,000), carbonic anhydrase (31,000) and soybean trypsin inhibitor (21,500).

Labeling with glucose-GAP resulted in one predominant band with an apparent molecular weight of approximately 55,000 (lane a). Protein components covalently attached to ouabain-GAP following labeling of human foreskin fibroblasts are shown in lane c. Here, also, a single predominant band is visible with an apparent molecular weight of approximately 60,000. Lane e is a control of dextranse alone exposed to identical incubation procedures while lanes b and d are controls for lanes a and c, respectively, in which dextranse treatment has been omitted.

DISCUSSION

Figure 5:
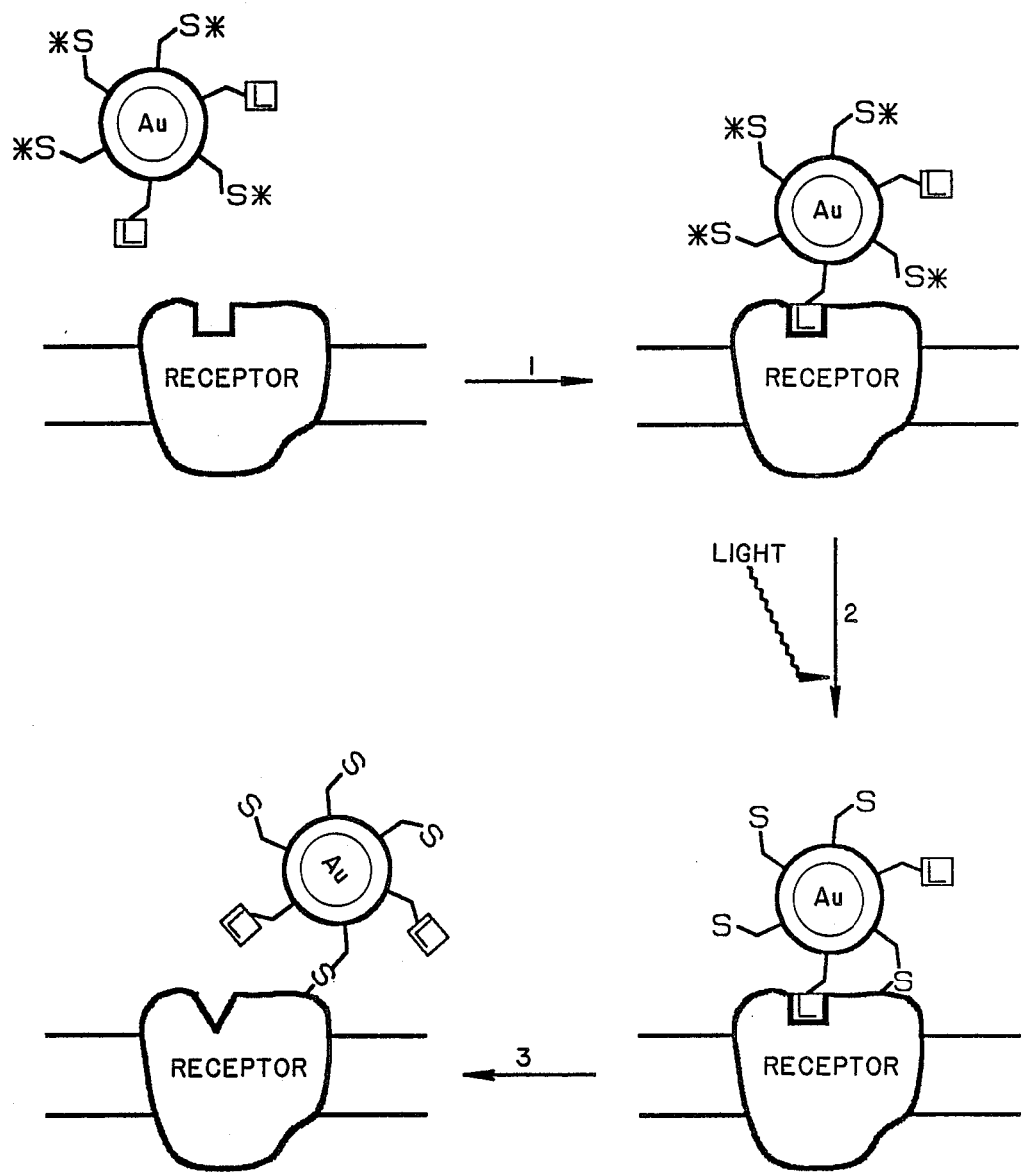
FIG. 5 is a schematic diagram of steps of a labeling method according to the present invention.
Figure 6:
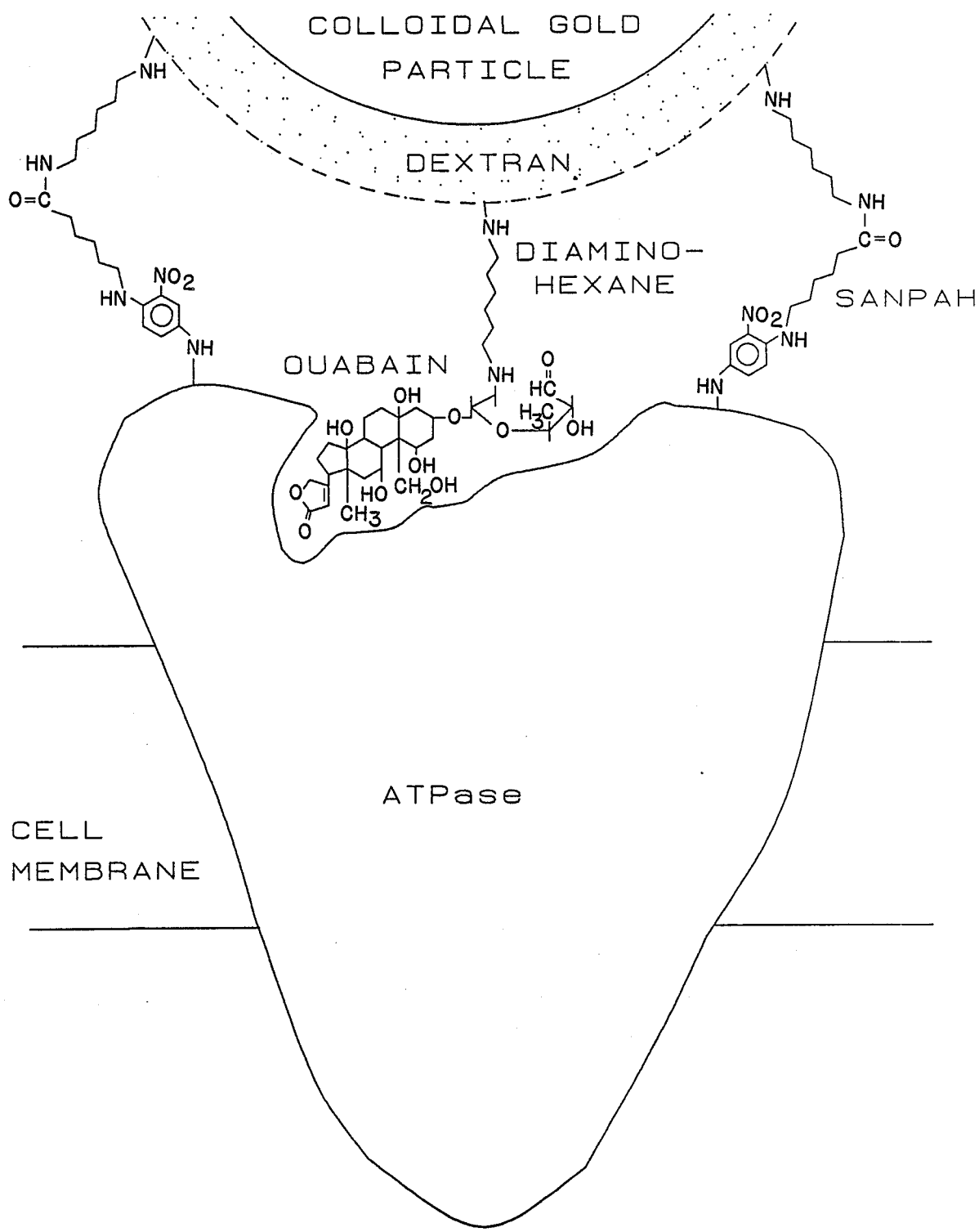
FIG. 6 is an enlarged view of the complex obtained after step 2 of FIG. 5 showing a probe crosslinked with SANPAH.

A schematic diagram representing the essential steps of the *affinity-gold labeling* method is shown in FIG. 5. Initial interaction between the gold-affinity probe (GAP) and the receptor is through the specific ligand (L) which allows for selective binding and directs the probe to the side of the receptor (step 1). In step 2, covalent attachment of the probe complex at or near the receptor site is accomplished by photoactivation of the crosslinking moieties (S). The bound GAP is then visualized by electron microscopy following standard procedures for fixation and dehydration (step 3). The covalent linkage between probe and receptor, as shown in FIG. 6, prevents loss of probe during these procedures.

The specificity of an affinity-gold probe is dictated by the nature of the ligand chemically incorporated into the probe matrix. The nature of these ligands can be quite varied and future utilization of a number of low molecular weight organic molecules with known against or antagonist activities for preparation of specific probes can be anticipated. These substances may include inhibitors, enzyme substrates or substrate analogs, hormones, pheromones, neurotransmitters, drugs and tumor promoters as discussed above. Regarding the versatility of this approach, it is of critical importance that these ligands be attached to the probe matrix with full retention of receptor binding capacity. The widely sued technique of affinity chromatography, which is also dependent upon coupling of ligands to a solid matrix with retention of full binding capacity, shows that this is possible in many cases. Many of the strategies developed for coupling of bio-active ligands with different functional groups to matrices for affinity chromatography may also be useful for preparation of GAPs.

In the present example, the specific ligands used were glucose and ouabain, resulting in glucose-GAP, a probe specific for the glucose transporter complex (and possibly other glucose receptors), and ouabain-GAP, a probe specific for the Na,K-ATPase. For both probes, labeling of erythrocytes and fibroblasts was found to be specific based on the following criteria: (1) Interaction of glucose-GAP and ouabain-GAP with the cell surface was blocked by the presence of excess competing ligand, i.e., glucose or glucose plus ouabain, respectively. (2) Binding of glucose-GAP was also blocked by cytochalasin B, a potent inhibitor of the glucose transporter [Sogin and Hinkle, "Characterization of the Glucose Transporter from Human Erythrocytes," *J. Supramol. Struct.* 8:447-453 (1978)]. (3) Ouabain-Gap was found to inhibit the Na,K-ATPase activity of a microsomal preparation of dog kidney cortex and inducing a morphological response in cultured human forskin fibroblasts, while SOD inhibited transepithelial short circuit currents across cultured monolayers of dog trachea epithelial cells, all in a manner similar to that of free added ouabain. The intrinsic affinity of the dextran-gold matrix for glucose receptors, which is due to the presence of terminal glucose residues in dextran, was not a problem since this interaction could easily be circumvented (if so desired) by addition of glucose to the labeling medium.

Labeling with the Na,K-ATPase-specific probe (ouabain-GAP) was found to be more efficient than labeling with a glucose-GAP. Human erythrocytes were used to quantitate labeling by both probes. Labeling by glucose-GAP as indicated by the number of silver piles observed on the cell surface accounts for less than 0.1 percent of the 300,000 or so glucose transporter copies present per erythrocyte [Mueckler et al., "Sequence and Structure of a Human Glucose Transporter," *Science* 229:941-945 (1985)]. Labeling by ouabain-GAP, however, accounts for approximately 50 percent of the 200-250 ouabain binding sites on the human erythrocyte [Erdmann and Hasse, "Quantitative Aspects of Ouabain Binding to Human Erythrocyte and Cardiac Membranes," *J. Physiol.* 251:671-682 (1975)]. This rather large difference in labeling efficiency is most likely explained by the difference in binding affinities of glucose and ouabain for their respective receptors. The dissociation constant for the glucose-glucose transporter complex has been reported as 50 mM [Sogin and Hinkle], while the ouabain-ATPase complex has a dissociation constant of 2.8 nM [Erdmann and Hasse]. Since the concentration of probe-associated ligand is in the micromolar range under our labeling conditions, this means that only a small fraction of the available glucose binding sties is occupied at any given time ($[L] << K_D$), whereas the occupancy of the ouabain binding sites is much higher ($[L] >> K_D$). Evidently, for optimal labeling, the affinity of the specific ligand for the receptor should be high. In cases where a high-affinity agonist or antagonist is not available and cell damage is minimal, labeling efficiency may be improved by repetitive cycles of labeling and irradiation.

Previous studies have reported a number of difficulties in localization of receptors employing small molecule ligands. For example, specifically bound radiolabeled ouabain can be lost from tissue due to ligand solubility during washing or dehydration or due to the chemical modification of the receptor during procedures commonly used in sample preparation for microscopy [Stirling, "Radioautographic Localization of Sodium Pump Sites in Rabbit Intestine," *J. Cell Biol.* 53:704-714 (1972); Stirling, "High-Resolution Autoradiography of $^3$H-Ouabain Binding in Salt Transporting Epithelia," *J. Microscopy* 106:145-157 (1976)].

To circumvent these potential problems, the probes described in the present example have a photo-activated crosslinking agent (SANPAH) incorporated into the probe matrix. Following receptor-specific interaction, covalent attachment of the probe is achieved through photo-activation of the arylazido group of the SANPAH generating a highly reactive nitrene (step 2 of FIG. 5). The presence of the SANPAH was found to be important since photolysis of the probes prior to labeling reduces (in the case of glucose-GAP) or virtually eliminates (in the case of ouabain-GAP) labeling observed by these probes (data not shown). Omitting the photolysis step similarly results in reduced labeling dependent on which probe is used. The efficiency of labeling is also dependent on this step since not every probe-receptor complex will produce a stable covalent bond upon irradiation.

The receptor-probe complex produced by photoactivation of receptor-associated GAPs can be isolated by taking advantage of the high density of the incorporated colloidal gold particle. Once isolated, e.g. by sedimentation, the polypeptide composition of the receptor-probe complex can be determined. The work described here shows that labeling with glucose-GAP or ouabain-GAP is selective in that the composition of the polypeptides covalently attached to the probes is relatively simple.

Labeling with glucose-GAP produces one main band in SDS-PAGE and the estimated molecular weight of this polypeptide component (55kD) coincides with that reported for the murine fibroblast glucose transporter [Kasahara and Hinkle, "Reconstitution and Purification of the D-Glucose Transporter from Human Erythrocytes," *J. Biol. Chem.* 252:7384–7390 (1977)]. Ouabain-GAP also labels one main polypeptide component with a MW of approximately 60 kD. This MW is similar to that of the $\beta$-subunit of the Na,K-ATPase complex which has been proposed to be comprised of 120 kD catalytic $\alpha$-subunits, 64 kD glycoprotein $\beta$-subunits and possibly 12 kD proteolipid $\gamma$-subunits [Craig and Kyte, "Stoichiometry and Molecular Weight of the Minimum Asymmetric Unit of Canine Renal Sodium and Potassium Ion-Activated Adenosine Triphosphatase," *J. Biol. Chem.* 255:6262–6269 (1980); Reeves et al., "Isolation and Characterization of (Na,K)-ATPase Proteolipid," *Biochem. Biophys. Res. Commun.* 95:1591–1598 (1980)]. These results suggest that affinity-gold labeling can provide some information concerning the polypeptide composition of cell surface receptors. However, dependent upon the particular combination of probe and cell type examined, the polypeptide composition may be more complex and include membrane components that are not themselves part of the receptor complex but become labeled due to their close proximity to the receptor site.

Following covalent attachment of the probe, ultrastructural localization of the affinity-gold probe is no longer dependent on the stability of specific ligand-receptor interactions, thus allowing for the use of standard sample preparation without loss of probe (step 3 of FIG. 5). Visualization of the probes by electron microscopy takes advantage of the high density of the 6 nm colloidal gold particles at the core of the probe matrix. The small size of the colloidal gold was selected to reduce potential problems caused by stearic hindrance which would block effective receptor-ligand interaction. Due to the density of the colloidal gold, these particles can easily be seen by TEM [Horisberger and Rosset, "Colloidal Gold. A Useful Marker for Transmission and Scanning Electron Microscopy," *J. Histochem. Cytochem.* 25:295–305 (1977)]. Resolution of the probes by SEM, however, requires enlargement of the colloidal gold particles which can be accomplished by silver enhancement. SEM requires particle enlargement since visualization of the probe is based upon topographical relief after Au:Pd coating. Extensive particle enlargement, however, may result in fusion of individual silver piles which masks the absolute number of probe particles visible on the cell surface.

This example most specifically concerns probes for cell surface labeling with the following attributes: (1) Selectivity based on functional ligand-receptor interactions; (2) Visibility by high-resolution electron microscopy; (3) Covalent attachment of the probe at the specific binding site; (4) Possibility of isolating and analyzing the membrane components to which the probe is attached. The results obtained here with the two probes, glucose-GAP and ouabain-GAP, show that these requirements are met by using colloidal gold particles coated with a derivatized dextran matrix to which specific ligands and photoactivated crosslinkers are attached. Visualization of the colloidal gold core of an attached probe by SEM or TEM allows for various structural aspects of cell morphology to be investigated, including the lateral distribution and dynamics of functional receptors at the plasma membrane. With the ability to simultaneously follow cellular responses stimulated or inhibited by interaction of the probe ligand with the surface receptor, structure-function correlations can be made. The use of gold-affinity probes offers cross-species and cross-tissue capabilities and should provide a complementary approach to current cytochemical, immunocytochemical and autoradiographic methods.

While we have shown and described the principles of our invention with reference to preferred embodiments, it should be apparent to those persons skilled in the art that such invention may be modified in arrangement and detail without departing from such principles. We claim as our invention all such modifications as come within the true spirit and scope of the following claims.

We claim:

1. A method for labeling cellular material with colloidal sized particles, the method comprising:
   providing a probe which includes a colloidal sized particle, a crosslinking agent and a ligand bound to the particles;
   contacting the probe with a cellular material having a receptor for the ligand so that the ligand joins with a receptor of the cellular material; and
   inducing the crosslinking agent to react with the cellular material to provide a covalent bond between the probe and the cellular material.

2. The method of claim 1 wherein the ligand and crosslinking agent are attached to the particle by a polymer having functional groups suitable for attachment of both the ligand and the crosslinking agent.

3. The method of claim 2 wherein the polymer is a water soluble polysaccharide or a derivative thereof having pendant functional groups.

4. The method of claim 1 wherein the ligand is attached to the particle by dextran.

5. The method of claim 1 wherein the crosslinking agent has a functional group which can be induced to react with the cellular material by photo irradiation.

6. The method of claim 1 wherein the crosslinking agent is 6(4'-azido-2'-nitrophenylamino) hexanoyl (SANPAH).

7. The method of claim 1 wherein the ligand is ouabain.

8. The method of claim 1 wherein the ligand is a polymer that:
   has a terminal glucose residue;
   is water soluble;
   has a sufficient number of functional groups to allow for covalent attachment of crosslinking moieties; and
   is capable of binding to the particle.

9. The method of claim 1 wherein:
   the ligand is attached to the particle by a dextran derivative;
   the crosslinking agent is 6(4'-azido-2'-nitrophenylamino) hexanoyl (SANPAH), which is bound to the dextran derivative; and
   the colloidal sized particle is gold.

10. A specimen of cellular material prepared for study by the method of claim 1.

11. The method of claim 1 wherein the colloidal sized particle is an electron dense particle.

12. The method of claim 11 wherein the particle is a heavy metal.

13. The method of claim 12 wherein the particle is gold.

14. A probe for labeling cellular material with a colloidal sized particle, the probe comprising:
   a colloidal sized particle;
   a ligand capable of joining with a receptor on cellular material; and
   a cross linking agent capable of reacting with the cellular material to provide a covalent bond between the probe and the cellular material.

15. The probe of claim 14 wherein the ligand is attached to the particle by dextran.

16. The probe of claim 14 wherein the crosslinking agent has a functional group which can be induced to react with the cellular material by photo irradiation.

17. The probe of claim 14 wherein the crosslinking agent is 6(4'-azido-2'-nitrophenylamino) hexanoyl (SANPAH).

18. The probe of claim 14 wherein the ligand is ouabain.

19. The probe of claim 14 wherein the ligand is a polymer that:
   has a terminal glucose residue;
   is water soluble;
   has a sufficient number of functional groups to allow for covalent attachment of crosslinking moieties; and
   is capable of binding to the particle.

20. The probe of claim 14 wherein:
   the crosslinking agent is 6(4'-azido-2'-nitrophenylamino) hexanoyl (SANPAH), which is bound to the dextran derivative; and
   the colloidal sized particle is gold.

21. The probe of claim 14 wherein the ligand and crosslinking agent are attached to the particle by a polymer having functional groups suitable for attachment of the ligand and the crosslinking agent.

22. The method of claim 21 wherein the polymer is a water soluble polysaccharide or a derivative thereof having pendant functional groups.

23. The probe of claim 14 wherein the colloidal sized particle is an electron dense particle.

24. The probe of claim 23 wherein the particle is a heavy metal.

25. The probe of claim 24 wherein the particle is gold.

26. A method for isolating molecules or complexes of molecules having receptors, the method comprising:
   labeling target molecules or a complex of molecules by contacting the molecule or the complex with the probe according to claim 14 and inducing the crosslinking agent to react with the molecule or complex to provide a covalent bond between the probe and the molecule or the complex; and
   separating the labeled molecule or the complex by action on a physical parameter of the probe.

27. A method for making a probe for labeling cellular material with colloidal-sized particles, the method comprising binding a ligand and crosslinking agent to a colloidal-sized particle, the crosslinking agent being capable of reacting with cellular material to provide a covalent bond between the probe and the cellular material.

28. The method of claim 27 wherein the ligand and the crosslinking agent are attached to the particle by dextran.

29. The method of claim 27 wherein the crosslinking agent has a functional group which can be induced to react with the cellular material by the application of photo irradiation.

30. The method of claim 27 wherein the crosslinking agent is 6(4'-azido-2'-nitrophenylamino) hexanoyl (SANPAH).

31. The method of claim 27 wherein the ligand is ouabain.

32. The method of claim 27 wherein the ligand is a polymer that:
   has a terminal glucose residue;
   is water soluble;
   has a sufficient number of functional groups to allow for covalent attachment of crosslinking moieties; and
   is capable of binding to the particle.

33. The method of claim 27 wherein the ligand is selected from the group consisting of biogenic amine neurotransmitters, neurologically active amino acids, neuropeptides, hormones, growth factors, ion channel blockers, enzyme substrates or inhibitors, drugs and tumor promoters, oligonucleotides and complementary DNA fragments.

34. The method of claim 27 wherein:
   the ligand and the crosslinking agent are attached to the particle by a dextran derivative;
   the crosslinking agent is 6(4'-azido-2'-nitrophenylamino) hexanoyl (SANPAH); and
   the colloidal sized particle is gold.

35. The method of claim 27 wherein the ligand and the crosslinking agent are attached to the particle by a polymer having functional groups suitable for attachment of the ligand and the crosslinking agent.

36. The method of claim 35 wherein the polymer is a water soluble polysaccharide or a derivative thereof having pendant functional groups.

37. The method of claim 27 wherein the colloidal sized particle is an electron dense particle.

38. The method of claim 37 wherein the particle is a heavy metal.

39. The method of claim 38 wherein the particle is gold.

* * * * *